US009974476B2

United States Patent
Aron et al.

(10) Patent No.: US 9,974,476 B2
(45) Date of Patent: May 22, 2018

(54) HANDHELD CORDLESS NON-NUTRITIVE SUCK ASSESSMENT DEVICE

(71) Applicant: Innara Health, Inc., Olathe, KS (US)

(72) Inventors: Kenneth Aron, Olathe, KS (US); David L. Stalling, Olathe, KS (US); John Kean, Olathe, KS (US); Allen Ingling, Olathe, KS (US)

(73) Assignee: Innara Health, Inc., Olathe, KS (US)

( * ) Notice: Subject to any disclaimer, the term of this patent is extended or adjusted under 35 U.S.C. 154(b) by 397 days.

(21) Appl. No.: 14/160,254

(22) Filed: Jan. 21, 2014

(65) Prior Publication Data

US 2014/0207024 A1 Jul. 24, 2014

Related U.S. Application Data

(60) Provisional application No. 61/754,808, filed on Jan. 21, 2013.

(51) Int. Cl.
*A61B 5/00* (2006.01)
*A61J 17/00* (2006.01)

(52) U.S. Cl.
CPC ............ *A61B 5/4542* (2013.01); *A61B 5/682* (2013.01); *A61B 5/6803* (2013.01);
(Continued)

(58) Field of Classification Search
CPC ....... A61B 5/038; A61B 5/682; A61B 5/4542; A61B 5/6896
(Continued)

(56) References Cited

U.S. PATENT DOCUMENTS 4,232,687 A * 11/1980 Anderson-Shanklin . A61B 5/03
600/590
5,830,235 A * 11/1998 Standley ................ A61B 5/038
40/455
(Continued)

FOREIGN PATENT DOCUMENTS

CN          101080195 B1    11/2012
EP            1850226 A1    10/2007
(Continued)

OTHER PUBLICATIONS

Pereira, Miguel, Octavian Postolache, and Pedro Girão. "A Smart Measurement and Stimulation System to Analyze and Promote Non-Nutritive Sucking of Premature Babies." Measurement Science Review 11.6 (2011): 173-180.*
(Continued)

*Primary Examiner* — Michael C Stout
*Assistant Examiner* — Nicholas E Kolderman
(74) *Attorney, Agent, or Firm* — Polsinelli PC

(57) ABSTRACT

A handheld device detects and measures orofacial activity, including oral cavity pressure and one or more compressions, deformations, displacements, or deflections of a pacifier engaged to the device. The compressions, deformations, displacements, or deflections of the pacifier refer to changes in the shape of the pacifier, caused by patient, relative to an initial state of the pacifier. The device translates the oral cavity pressure and compressions into an electrical signal, digitizes the electrical signal, and performs analytical processing of the digitized signal to extract physiological artifacts salient to the patient's ability to orally feed using a software application executing on a processor within the device. The device automates and simplifies the assessment of a patient's readiness to orally feed by presenting graphical
(Continued)

and numeric scores for organization and effort of non-nutritive suck.

25 Claims, 10 Drawing Sheets

(52) U.S. Cl.
CPC .......... *A61B 5/6896* (2013.01); *A61B 5/7282* (2013.01); *A61B 5/742* (2013.01); *A61B 5/0004* (2013.01); *A61B 5/7225* (2013.01); *A61B 5/7475* (2013.01); *A61B 2503/045* (2013.01); *A61B 2560/0204* (2013.01); *A61B 2562/0247* (2013.01); *A61J 17/001* (2015.05)

(58) Field of Classification Search
USPC ........................................ 600/300, 301, 590
See application file for complete search history.

(56) References Cited

U.S. PATENT DOCUMENTS

| | | | |
|---|---|---|---|
| 6,033,367 A | | 3/2000 | Goldfield |
| 7,435,232 B2 | | 10/2008 | Liebschner |
| 7,917,201 B2 | | 3/2011 | Gozani et al. |
| 8,157,731 B2 | | 4/2012 | Teller et al. |
| 8,226,579 B2 | | 7/2012 | Barlow et al. |
| 8,251,926 B2 | | 8/2012 | Barlow et al. |
| 2004/0019382 A1 | | 1/2004 | Amirouche et al. |
| 2006/0041731 A1* | 2/2006 | Jochemsen | G06F 12/0223 711/170 |
| 2006/0074354 A1 | | 4/2006 | Barlow et al. |
| 2006/0079814 A1 | | 4/2006 | Barlow et al. |
| 2008/0039778 A1* | 2/2008 | Goldie | A61B 5/038 604/67 |
| 2008/0077183 A1 | | 3/2008 | Cohen |
| 2008/0287751 A1* | 11/2008 | Stivoric | A61B 5/0205 600/301 |
| 2009/0156967 A1 | | 6/2009 | Cohen |
| 2009/0222214 A1* | 9/2009 | Barlow | A61B 5/038 702/19 |
| 2010/0016675 A1* | 1/2010 | Cohen | A61B 5/6896 600/300 |
| 2010/0075285 A1* | 3/2010 | Stalling | A61J 17/00 434/258 |
| 2010/0131454 A1* | 5/2010 | Kaplan | A23L 33/40 706/54 |
| 2011/0060252 A1 | | 3/2011 | Simonsen et al. |
| 2011/0087078 A1* | 4/2011 | Zemel | A61B 5/4288 600/300 |
| 2012/0209147 A1* | 8/2012 | Barlow | A61B 5/038 600/590 |
| 2012/0209148 A1 | | 8/2012 | Barlow et al. |
| 2012/0232801 A1 | | 9/2012 | Kaplan et al. |
| 2013/0091642 A1* | 4/2013 | Dykes | A46B 15/0008 15/22.1 |

FOREIGN PATENT DOCUMENTS

| | | |
|---|---|---|
| EP | 1786319 B1 | 10/2012 |
| GB | 1206014 A | 9/1970 |
| JP | 2007-319662 | 12/2007 |
| WO | 2006026623 A2 | 3/2006 |
| WO | 2006081376 A1 | 8/2006 |
| WO | 2008067607 A1 | 6/2008 |

OTHER PUBLICATIONS

PCT/US14/12350 International Search Report and Written Opinion dated May 21, 2014 (11 pages).
Barlow et al, "Synthetic orocutaneous stimulation entrains preterm infants with feeding difficulties to suck." J Perinatol, 2008, pp. 541-548, vol. 28, No. 8.
Goldfield et al.; "Coordination of Sucking, Swallowing, and Breathing and Oxygen Saturation During Early Infant Breast-feeding and Bottle-feeding"; Pediatric Research; vol. 60;/ No. 4; pp. 450-455; Oct. 2006.
Poore et al., "Respiratory treatment history predicts suck pattern stability in preterm infants." J Neonatal Nurs, 2008, pp. 185-192, vol. 14, No. 6.
European Application Serial No. 09250464.6, Office Action dated Mar. 22, 2012, 11 pgs.
Estep et al., "Non-Nutritive Suck Parameter in Preterm Infants with RDS." J Neonatal Nurs, 2008, pp. 28-34, vol. 14, No. 1.
Stumm et al., "Respiratory Distress Syndrome Degrades the Fine Structure of the Non-Nutritive Suck in Preterm Infants." J Neonatal Nurs, 2008, pp. 9-16, vol. 14, No. 1.
Vantipalli et al.; Somatosensory entrainment of suck in preterm infants: NTrainer CNL Technical Research Report; 2006; 3:1-23 entire document.
PCT/US2013/038405 International Search Report and Written Opinion dated Jul. 11, 2013; (10 pages).
PCT/US2013/038410 International Search Report and Written Opinion dated Jul. 15, 2013 (8 pages).
PCT/US13/38400 International Search Report and Written Opinion dated Jul. 19, 2013 (15 pages).

* cited by examiner

HANDHELD CORDLESS NON-NUTRITIVE SUCK ASSESSMENT DEVICE

CROSS REFERENCE TO RELATED APPLICATIONS

This application claims the benefit of priority to U.S. Provisional Application No. 61/754,808, filed Jan. 21, 2013, entitled "Handheld Cordless Non-Nutritive Suck Assessment Device," the entire contents of which are hereby incorporated herein by reference.

FEDERALLY SPONSORED RESEARCH OR DEVELOPMENT

N/A

FIELD

The present systems and methods relate generally to a cordless handheld device that detects and analyzes orofacial activity based on oral cavity pressure and compressions or deflections of an associated pacifier. The device can receive and analyze data that can be used to train an infant to feed.

BACKGROUND

Neonates born prematurely and/or with certain disease conditions may have an impaired ability to feed orally. Attempting to orally feed a neonate with impaired ability may result in aspiration of the fluid, physically injuring the neonate. The ability to objectively assess a neonate's readiness and ability to take oral nutrition and avoid patient injury is the subject of extensive training, specialization, and controversy in the neonatal clinical community.

Previous efforts to detect and measure orofacial activity often involved a manual detection or the use of a bottle or pacifier device wired to a computer on a stand. Manual assessment of orofacial activity has a number of drawbacks including but not limited to the variance in the amount of motion (amplitude) and rhythm (frequency) as detected and determined from therapist to therapist, or even by the same individual. As a result, extensive and costly training and experience are required for a therapist to be proficient at providing manual stimulation and assessment.

Similarly, devices physically wired to a computing device have drawbacks as well. These include the requirement to relocate the patient to a position proximal to the computer which may be difficult or ill advised for some neonatal patients. Alternately, the computing device may be brought near the patient; however, this requires the introduction of bulky wheeled equipment into a potentially crowded and tranquil environment.

Therefore, a need exists for a highly portable, and compact automated system and method of using the system to assess a patient's natural NNS pattern and to provide precise and beneficial tactile stimulus to correct and organize the patients NNS pattern in a low-cost, handheld, NNS assessment device.

SUMMARY

Briefly described, and according to one embodiment, aspects of the present disclosure generally relate to a handheld cordless device for assessing a non-nutritive suck of a patient. The non-nutritive suck (NNS) is a motor behavior that can be observed and used to make inference about brain development and organization in patients. In one embodiment, the device includes a device housing containing a non-nutritive suck assessment system. The non-nutritive suck assessment system further includes one or more transducer to sense a pacifier's displacement caused by the patient and oral cavity pressure caused by the patient. The one or more transducer also generates an electrical signal in response to at least one compression of the pacifier and the oral cavity pressure. The system includes an analog to digital convertor to convert the electrical signal to a digital signal that is received at a processor. Memory is used to store data collected from the pacifier and a suck assessment application that also includes instructions executable by the processor. Importantly, the device collects data allowing for assessment of whether an infant can breastfeed. The device may also be useful for training the infant to feed.

The device includes one or more switches to control the operation of the device, execution of the software application, and a display of assessment data on the display device. The handheld device also includes an internal power source, the display device that is engaged to the device housing, and at least one status indicator light.

In various aspects, the device is cordless and includes a wireless transceiver to communicate with another computing device. Included with the device is at least one signal conditioning circuit to filter and amplify the electrical signal generated by the one or more transducer. The power supply for the device may be a rechargeable battery that is in communication with a battery charging circuit configured to engage an external power supply.

In other aspects, the handheld device includes a pacifier adaptor that defines a lumen and has a first end in fluid communication with the one or more transducer engaged to the device housing and second end in fluid communication with the pacifier. The pacifier adaptor can be of a variety of lengths, but generally has a length between about 2.125" and 2.25" to provide a sterile barrier between the handheld device and patient. In addition, the display device may be an alphanumeric display and may be integrated with the device housing.

The suck assessment application may have a number of modules and be stored on a persistent random access memory. The modules may include a self-test module to perform a Power-On Self-Test, an error-detection module to detect an error in an operation of the suck assessment application and to notify a user of the error. The device includes a data collection module to receive patient oral feeding activity data within the digital signal, a data analysis module to analyze the patient oral feeding activity data and to determine at least one patient performance metric, and an output module to generate one or more data displays on the display device. The patient performance metric may include a peak area under burst, an average area under burst, an active-quiescent ratio, a spatio-temporal index, a rate of bursts per minute, a rate of non-nutritive suck events per minute, a rate of non-nutritive suck events per burst, or combinations thereof. The patient performance metric is used to analyze whether an individual can feed on their own.

According to one embodiment, a method includes using a handheld cordless device for assessing a non-nutritive suck of a patient. The method includes contacting the pacifier with the patient and actuating the control button to collect oral feeding activity data at the processor.

The method also includes analyzing the oral feeding activity data to identify at least one metric of the oral feeding activity. The metric is at least one member of a group consisting of a peak area under burst, an average area under burst, an active-quiescent ratio, a spatio-temporal index, a rate of bursts per minute, a rate of non-nutritive suck events per minute, a rate of non-nutritive suck events per burst, and combinations thereof. The performance metric is displayed on the display device.

Another method for assessing a non-nutritive suck of an infant patient using a handheld device having a non-nutritive suck assessment system includes actuating a control button to initiate execution of a non-nutritive suck assessment application on a processor of the handheld device and contacting a pacifier engaged to the handheld device with the infant patient. The method also includes sensing patient oral feeding activity at a data collection module of the non-nutritive suck assessment application. The patient activity is identified by a signal generated by one or more transducer in communication with the pacifier.

Patient oral feeding activity data is collected at the data collection module of the non-nutritive suck assessment application and at least one patient performance metric is extracted from the patient oral feeding activity data at a data analysis module. The method also includes displaying patient performance data, which is based on the at least one patient performance metric, on a display of the handheld device.

In various other aspects, the methods may also include performing a power-on self-test before contacting the patient, actuating a first display control button to scroll through the displayed patient performance data in a first direction, actuating a second display control button to scroll through the displayed patient performance data in a second direction, and storing the patient performance data in a persistent random access memory of the non-nutritive suck assessment system. In addition, the various methods may also include exporting the patient performance data to another data storage device.

DETAILED DESCRIPTION

The embodiments disclosed herein relate to a handheld device for detecting and measuring orofacial activity, including oral cavity pressure and one or more compressions, deformations, displacements, or deflections of a pacifier engaged to the device. The compressions, deformations, displacements, or deflections of the pacifier refer to changes in the shape of the pacifier, caused by patient, relative to an initial state of the pacifier. In one embodiment, the device is configured to translate the oral cavity pressure and compressions into an electrical signal, digitize the electrical signal, and perform analytical processing of the digitized signal to extract physiological artifacts salient to the patient's ability to orally feed using a software application executing on a processor within the device. The device automates and simplifies the assessment of a patient's readiness to orally feed by presenting graphical and numeric scores for organization and effort of non-nutritive suck.

In various aspects, a disposable pacifier defining at least one orifice is engaged to the device to measure oral cavity vacuum synchronized with patient feeding motion. The device may be battery powered, cordless, lightweight, and compact to be used with a single hand similar to a feeding bottle.

Figure 1:
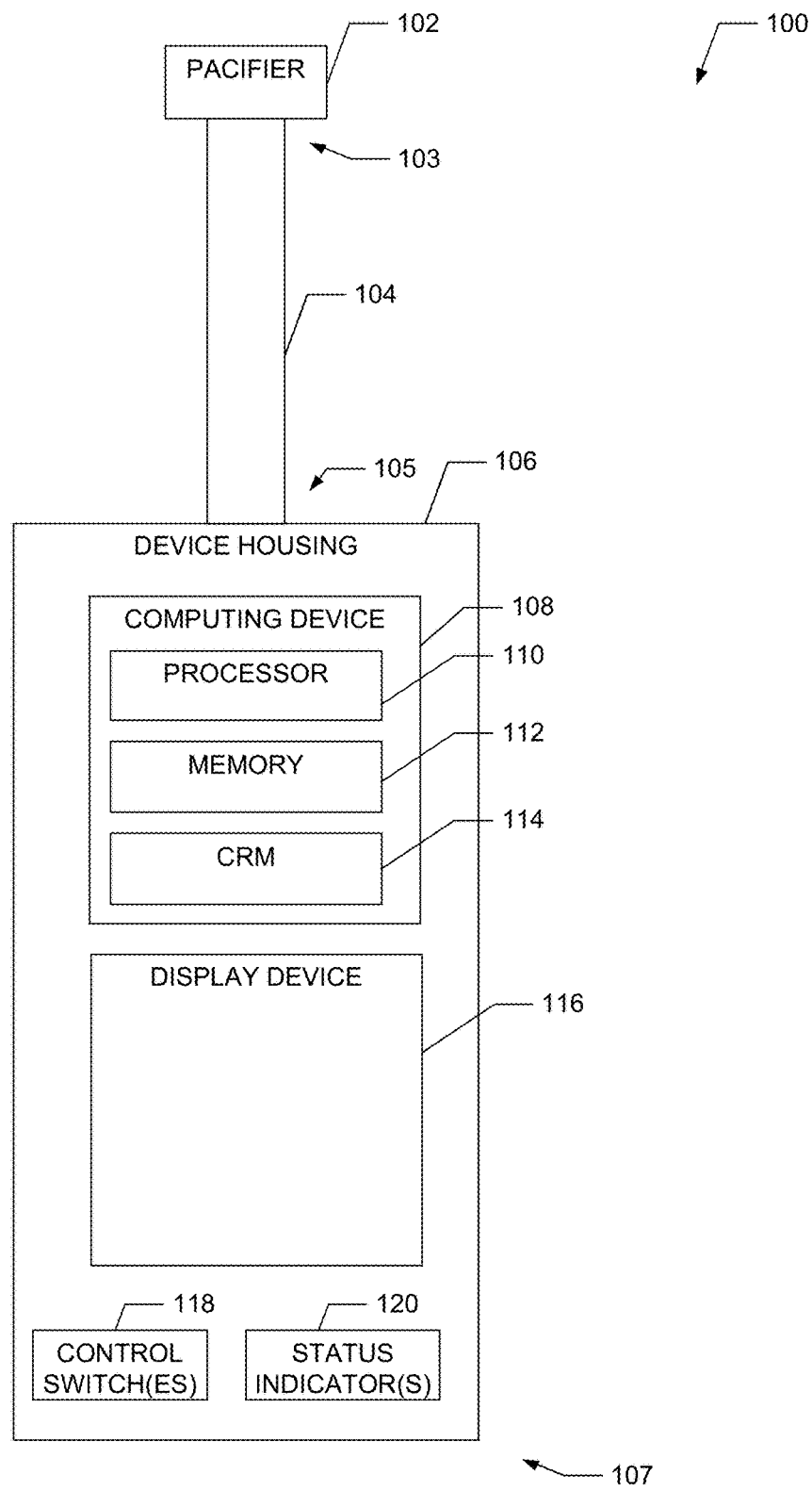
FIG. 1 is a block diagram of a handheld cordless non-nutritive suck assessment device according to one embodiment.
Figure 2:
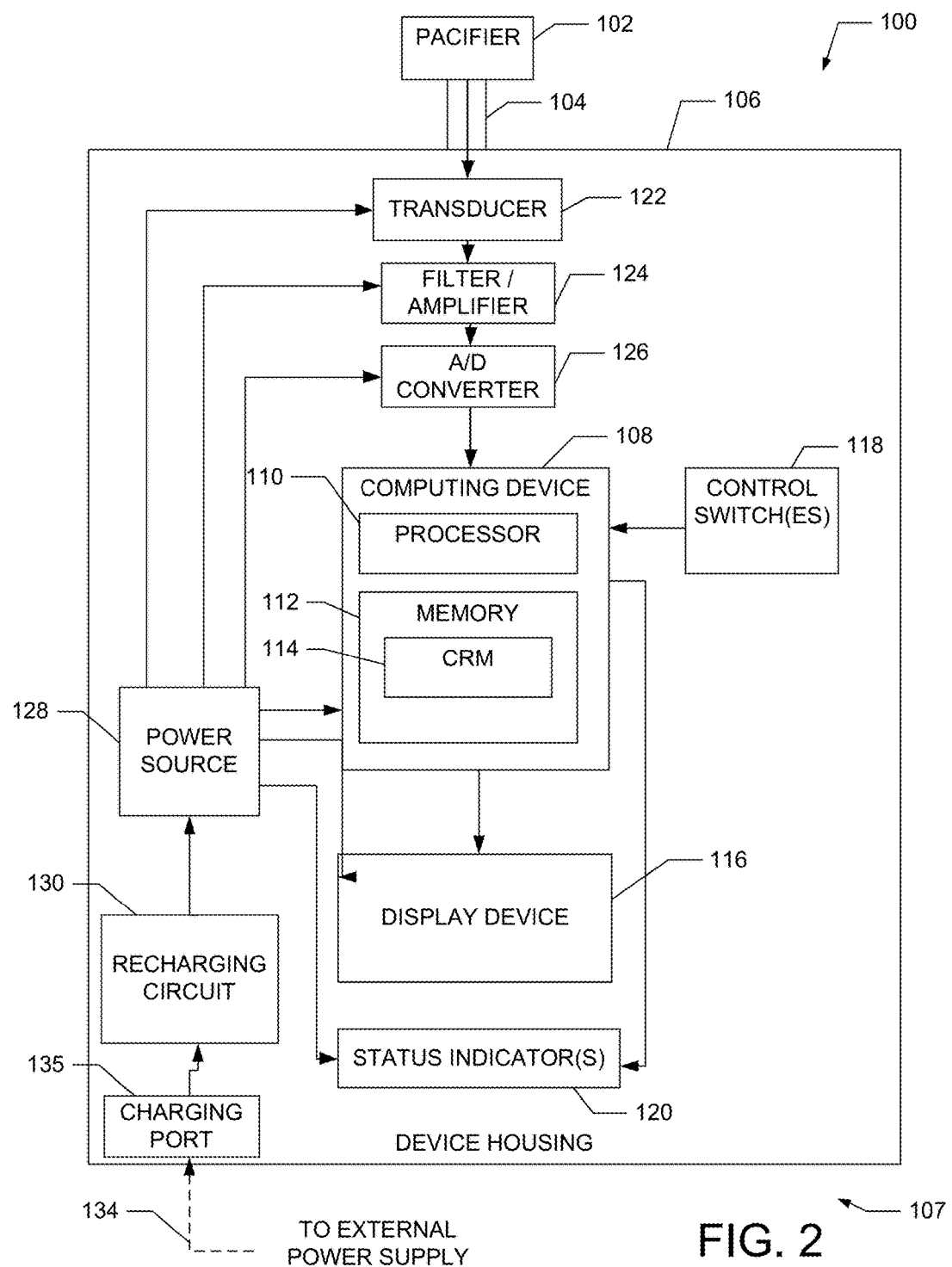
FIG. 2 is a schematic block diagram of a handheld cordless non-nutritive suck assessment device according to one embodiment.

FIGS. 1 and 2 are block diagrams of embodiments of the handheld non-nutritive suck (NNS) assessment device 100. Typically, the sucking of an infant or neonate is characterized by two basic forms of sucking. These include non-nutritive sucking when no nutrient (e.g. a food or a beverage) is involved, such as when using a pacifier, and nutritive sucking when a nutrient is ingested from a bottle or a breast. Mature nutritive sucking is defined as the rhythmic alternation of suction (i.e. negative oral cavity pressure that draws a nutrient into the mouth) and expression (i.e. the positive pressure generated by the compression of the nipple) that ejects the nutrient into the mouth.

Figure 11:
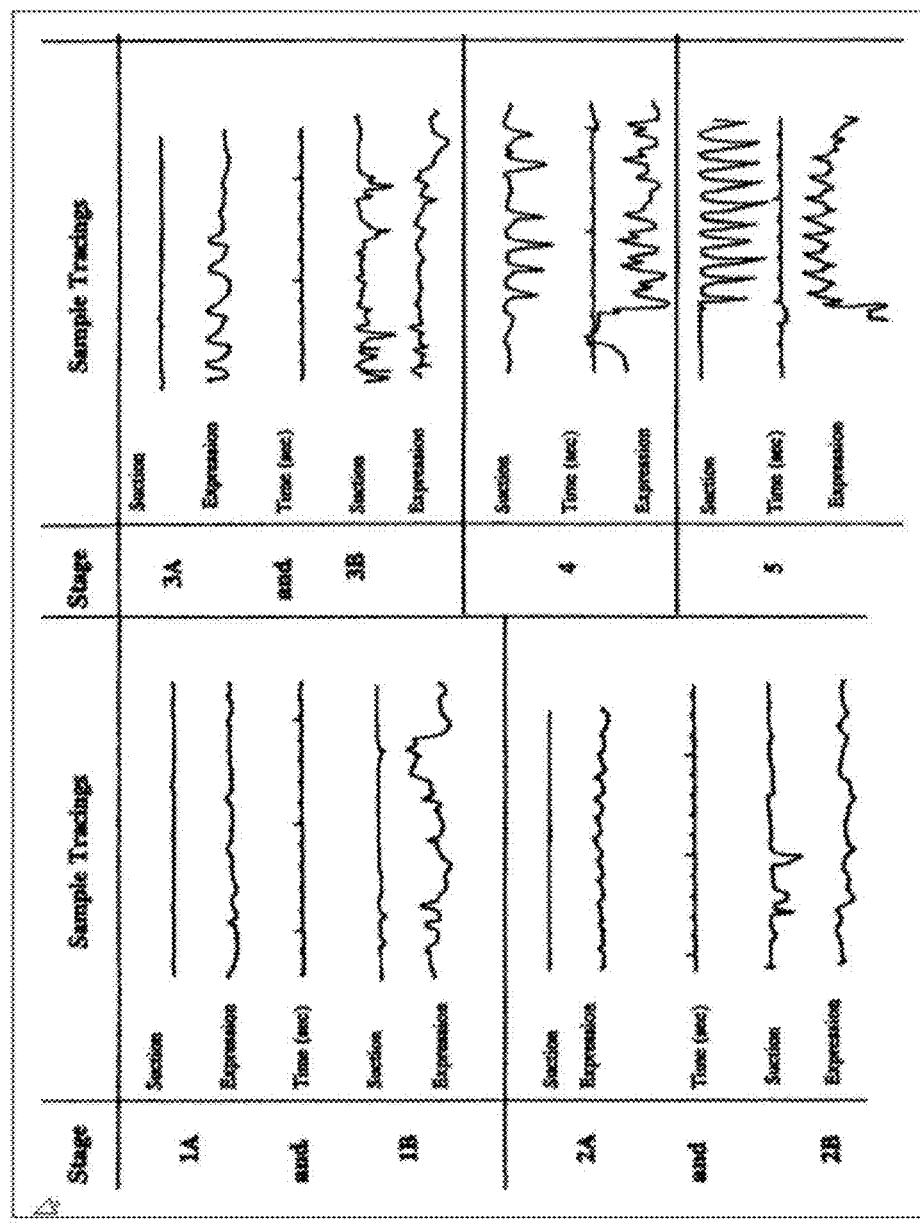
FIG. 11 illustrates a chart showing sample tracking corresponding to the each of the five defined stages of sucking.

The stages of suck maturation associated with negative oral cavity pressure are shown in FIG. 11. Mature sucking is developed according to the stages shown in FIG. 11. Sucking first begins with an emergence of an arrhythmic expression with no suction as shown in Stage 1. Expression becomes rhythmic and arrhythmic suction begins in stage 2. In stage 3, the suction becomes rhythmic. During stages 1-3, infants go from using only expression to alternating suction and expression within a feeding session. As the alternation of rhythmic suction/expression becomes more mature, suction amplitude increases along with the duration of bursts of sucking as seen in stages 4 and 5. This characterization of the progression of nutritive sucking correlates with postmenstrual age and with oral feeding performance as defined by the rate of milk transfer and the ability of an infant to complete a feeding within an allocated time.

A rhythmic NNS sucking pattern resembling that of mature nutritive sucking has been used as an indicator of readiness for oral feeding. Thus, NNS assessment and/or therapy is indirectly beneficial to the attainment of oral feeding skills and provides a good index of fundamental nutritive sucking skills associated with development of oral feeding skills, such as but not limited to suck, swallow, and respiration. The NNS assessment device 100 includes a pacifier 102 fitted on a pacifier adaptor 104 that is also engaged to a handheld device housing 106.

In various aspects, the pacifier 102 is a disposable pacifier that may be removably engaged to the pacifier adaptor 104. The pacifier 102 may be any suitable size and shape. As a first example, the pacifier 102 may be a smaller pacifier sized for an infant. Conversely, a larger pacifier sized for an adolescent or adult may be used. In one aspect, the pacifier configuration is determined by the patient undergoing the assessment.

According to one embodiment, the pacifier 102 includes a closed annular baglet engaged to a first pressure sensor. This first pressure sensor measures pressure based on compressions, deformations, displacements, and/or deflections of a pacifier. The pacifier 102 further may include a second sensing channel that is an open tubular channel engaged to a second pressure sensor. This second pressure sensor measures oral cavity pressure. The border of the mouth of the patient forms a seal against the pacifier 102 allowing negative pressure to be created. The emergence of negative oral cavity pressure (e.g., suction) has been found to represent a critical step in the development of readiness to feed as described herein and as shown in FIG. 11.

As such, a neonate pacifier may be engaged to the pacifier adaptor when the device 100 is used to assess the orofacial activity of a neonate including pacifier compression and oral cavity pressure, among other activity. As a result, the device 100 measures pressure in the oral cavity of the patient concurrently with pressure generated in the pacifier 102 by the patient's jaw and tongue.

The pacifier adaptor 104 is used to connect the pacifier 102 to the device housing 106. In particular, a distal end 103 of the pacifier adaptor 104 is engaged to the pacifier 102, while a proximal end 105 of the adaptor is engaged to the housing 106. In one embodiment, the distal end 103 engages the pacifier 102 via an interlocking friction-fit, while the proximal end 105 is threaded and threadably engaged to the device housing 106. Any other suitable connection means or combinations thereof may also be used.

Figure 5:
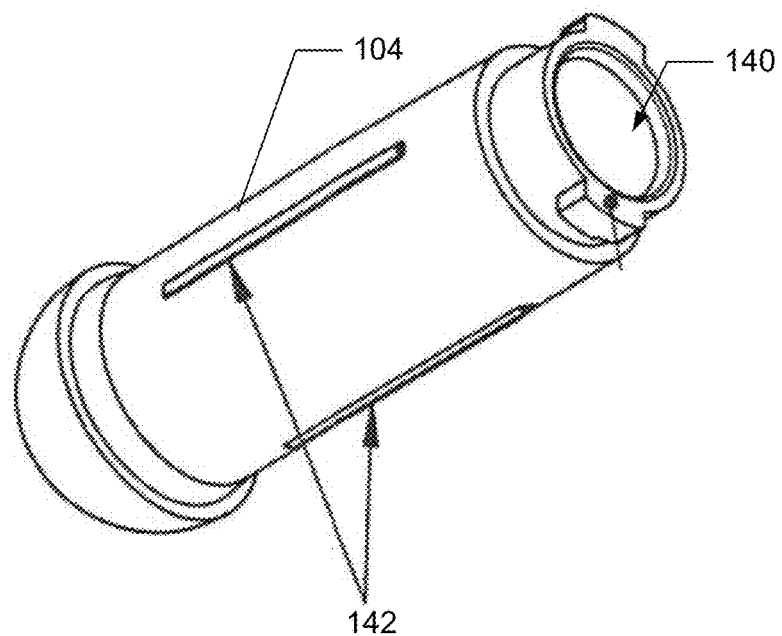
FIG. 5 is a perspective view of a pacifier adaptor for a handheld cordless non-nutritive suck assessment device according to one embodiment.

In one aspect, the pacifier adaptor 104 is of sufficient length to provide a sterile barrier between the pacifier 102 and the device housing 106. For example, the pacifier adaptor 104 may have a length in the range between about 1.5 inches to about 3 inches. The adaptor 104 defines a lumen having a diameter in a range between about 0.4 inches to about 0.6 inches. The lumen 140, as shown in FIG. 5, provides a pneumatic passageway between the pacifier 102 and a transducer 122, as shown in FIG. 2, located within the device housing 106. The lumen 140 defines a sufficient ballast volume of air within the lumen to maintain consistent pliability of the adaptor 104. In various aspects, the pacifier adaptor 104 may be disposable or suitable for sterilization and reuse. Although shown with a plurality of ribs 142 in FIG. 5, the pacifier adaptor 104 may have any of a variety of configurations to be compatible with and support any of a variety of commercially available pacifiers 102.

Figure 4:
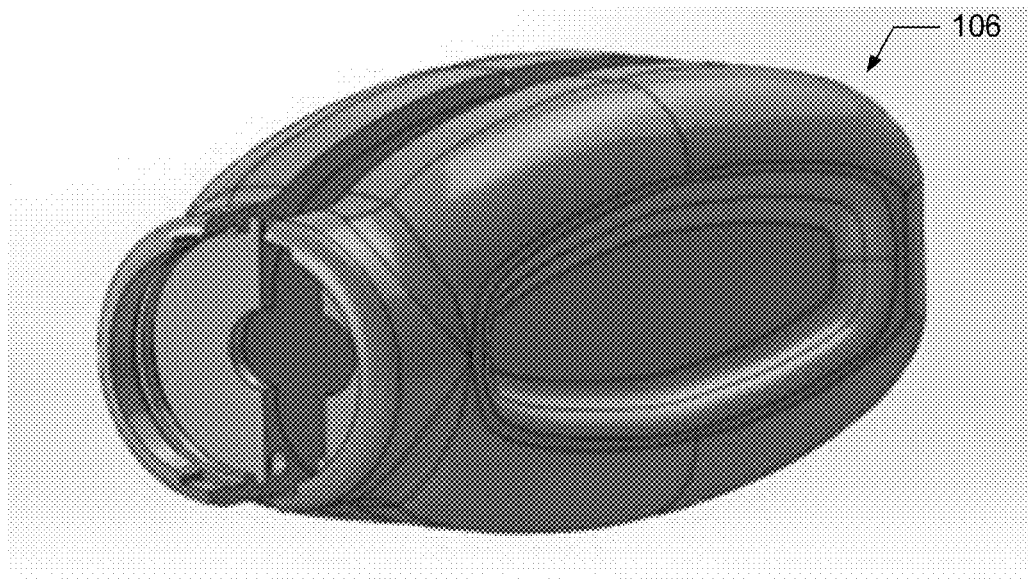
FIG. 4 is a perspective view of a housing for a handheld cordless non-nutritive suck assessment device according to one embodiment.

The device housing 106 houses a computing device 108, a display device 116, various control switches 118, and one or more status indicators 120. In one aspect, the housing 106 is sealed to prevent the intrusion of fluid into the housing. The housing may be sealed by any suitable method including but not limited to gaskets, washers, and other sealants. Although shown as having a generally rectangular configuration, the housing 106 may include one or more ergonomic configurations or features, such as the device housing 102, as shown in FIG. 4, to permit use by a single hand in a variety of orientations.

Figure 6:
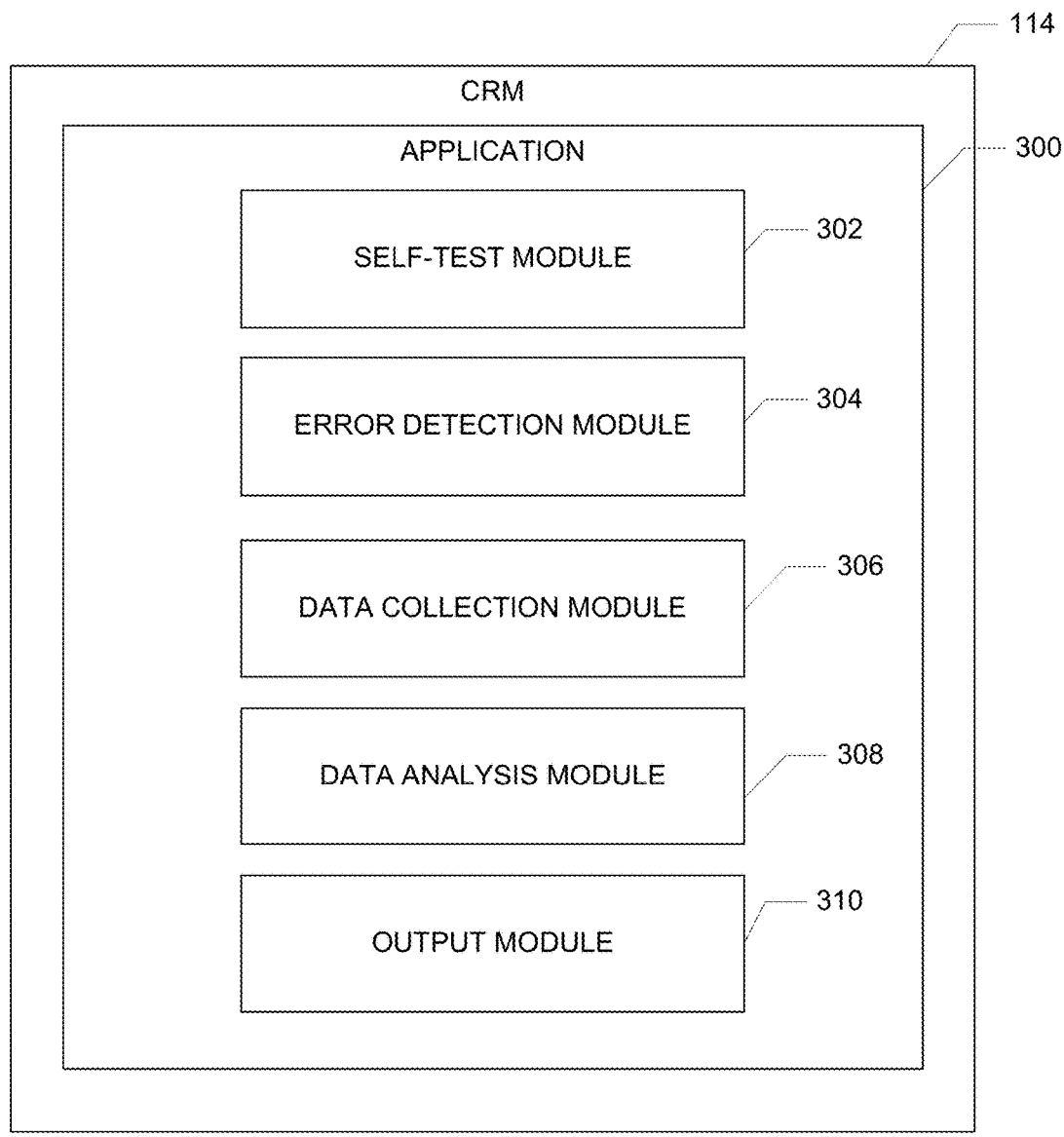
FIG. 6 is a block diagram of a computer readable medium and application executed on the handheld cordless non-nutritive suck assessment device according to one embodiment.

A computing device 108 including one or more processors 110 are within the device housing and receive data related to compressions, deformations, displacements, or deflections of the pacifier 102 (e.g., "pacifier pressure data") and data related to pressure in the patient oral cavity (e.g., "oral cavity pressure data") and perform analysis of the received data using a NNS assessment software application 300, as shown in FIG. 6. The computing device 108 also includes memory 112. The memory 112 may be any database, hard drive, flash drive, or other data storage device or structure. In one embodiment, the memory 112 is a persistent random access memory (RAM) that stores data collected by the device 100, provides a buffer for the processor 108, and stores at least one software application executable by the processor. In one embodiment, the processor 110 and memory 112 are hardware. In one aspect, the persistent RAM is immune to power losses.

The computing device 108 simultaneously receives the pacifier pressure data related to the compressions, deformations, displacements, or deflections from the pacifier 102 and the oral cavity pressure data related to the pressure in the patient oral cavity and stores the data in the memory 112 in a patient NNS suck profile (e.g., "patient profile"). The patient profile may be stored with one or more patient profiles associated with a patient as a patient profile history. The patient profile history may be stored in a database in the memory 112.

A patient profile includes data from a particular period of assessment collected from the NNS assessment device 100. According to an example embodiment, the particular period of assessment is two minutes. However, the particular period of assessment may be longer or shorter than two minutes. The computing device 108 also determines a ratio of pacifier pressure data to oral cavity pressure data and maxima and minima of the pacifier pressure data and the oral cavity pressure data and stores this information with the patient profile. The patient profile further includes a patient age at a time of assessment, and a name of the patient, among other data. The patient profile may be used to determine a patient readiness to feed and can be used to reduce aspiration risks during oral feeding.

The device housing 106 also includes a display device 116 for displaying data generated by the NNS assessment application 300 including information associated with a patient profile. In one aspect, the display device 116 is an alphanumeric display displaying patient performance metrics based on information from a current patient profile and patent profile history derived by the application 300 to the user. The display may also present various numeric performance values with textual labels. In one aspect, the display device is integrated into the device housing 106. The display device 116 may be a liquid-crystal display, a light-emitting diode (LED) display, a touch screen display, and the like.

The control switches 118 permit the user to interact with the device 100, the assessment application 300, and the display device 116. For example, one or more of the control switches 118 may allow the user to select and scroll through the displayed patient performance metrics. A single control switch may scroll through the displayed information in a single direction. Alternately, two or more control switches may be used to permit scrolling through the data in multiple directions. Another one of the control switches 118 may be a device control switch. For example, a device control switch may be used to start and stop the collection of data from the pacifier 102. In various embodiments, the control switches may be any suitable switch. By way of example and not limitation, the control switches 118 may be toggle switches, button switches, and/or capacitive buttons, among others.

The one or more status indicators 120 are lights or other suitable indicators that provide the user with a visual and/or audible indication of the status of one or more functions of the device 100. For example, status indicators 120 may be LED lights that inform the user of the power (off/on) status, the battery charge status, and/or patient activity collection status of the device 100. The status indicators 120 may be illuminated with a single color or they may be multi-colored to provide quick color-coded indications to the user. As another option, the one or more status indicators 120 may be one or more speaker for providing an audible tone or sound to inform the user of the power (off/on) status, the battery charge status and/or patient activity collection status of the device 100.

In various aspects, the device housing 106 is sufficiently small and maneuverable that it may be held and used in one hand. By way of example, the device 100 may have a length from a proximal end 107 of the device housing 106 to the distal end 103 of the pacifier adaptor 104 of approximately 3.5 inches and a total width of approximately 1.5 inches. Alternately, the size and shape of the device 100 may be altered by those having skill in the art, to any other suitable configuration and shape that may still be held and operated by a single hand, including but not limited to ergonomic configurations.

As shown in FIG. 2, the handheld NNS assessment device 100 may also include one or more signal detecting and conditioning components 122-126, an internal power source 128, and recharging components 130-134 for charging the internal power source. In one aspect, the NNS assessment device 100 includes one or more transducer 122 to detect deformation or displacement of the pacifier 102 caused by the patient and detect oral cavity pressure and to generate an orofacial activity signal. For example, the one or more transducer 122 generates the orofacial activity signal in response to a pressure change within the pacifier adaptor 104 that is caused by the deformation or displacement of the pacifier 102. As another example, the one or more transducer 122 generates the orofacial activity signal in response to a pressure change detected in the oral cavity of the patient.

In one aspect, the signal generated by the one or more transducer 122 is an analog signal where the instantaneous voltage of the signal varies continuously with the pneumatic pressure within the pacifier adaptor 104 and/or within the oral cavity of the patient. In this aspect, the analog signal correlates to the time-varying magnitude of deformation or displacement of the pacifier and the time-varying changes in pressure within the oral cavity of the patient. In another example, the one or more transducer 122 may include, or at least be in communication with a capacitive deformation sensor, to generate the orofacial activity signal in response to the deformation or displacement of the pacifier 102. In a further example, the one or more transducer 122 may include, or at least be in communication with another sensor to generate the orofacial activity signal in response to changes in pressure in the oral cavity of the patient. In various other aspects, any other sensing and/or and signal generating components may be used to generate the signal in response to deformation or displacement of the pacifier 102. The analog orofacial activity signal generated by the one or more transducer 122 is received at a signal filter or amplifier 124, where the signal undergoes signal processing, including filtering and amplification. The filtered and amplified signal is then received at an analog-to-digital (ND) converter 126, where the orofacial activity signal is converted to a digital signal by the computing device 108.

In one embodiment, the handheld NNS assessment device 100 includes a power source 128, such as a battery, to provide a direct current (DC) voltage to power the other components of the device. In one aspect, the power source 128 is a rechargeable battery. In this aspect, the handheld device 100 may also include a recharging circuit 130 that is configured to recharge the power source 128 through connection to an external power supply, as indicated by 132. For example, the handheld NNS assessment device 100 may be connected to the external power supply 132, through a power cord 134 that is connected to a charging port 136 of the device 100 and to the external power supply via a wall receptacle.

Figure 3:
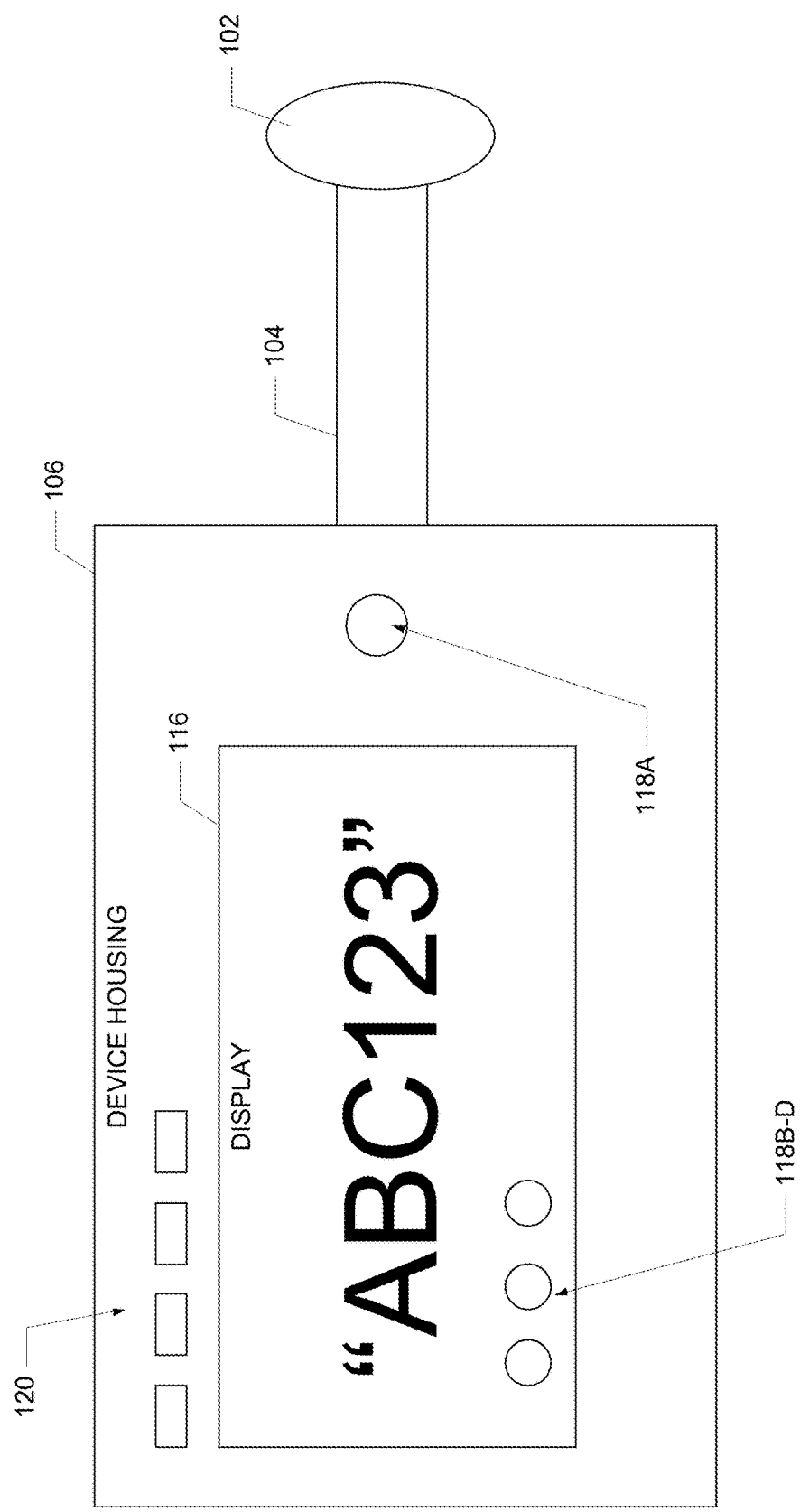
FIG. 3 is an exterior planar view of a handheld cordless non-nutritive suck assessment device according to one embodiment.

FIG. 3 is an exterior planar view of an embodiment of the handheld NNS assessment device 100. As shown, the control button 118A is a device control switch. The button 118A is located to permit a user of the device 100 to access and actuate the button using a single finger while in use. Similarly, control buttons 118B-D are located adjacent to the display device 116 and allow the user to scroll through the displayed data and/or any displayed menus. According to an embodiment, the displayed data may include information associated with a patient profile and/or a patient profile history. The control buttons 118B-D are also configured to permit the user to input data to the device 100.

In various embodiments, the device 100 may also include a wireless transceiver (not shown) to receive updates and share data with another computing device. For example, the transceiver may communicate over a Wi-Fi network. Alternately, the transceiver may be capable of transmitting and receiving data using the Bluetooth standard and other short-range wireless networking standards.

According to various aspects, as shown in FIGS. 1, 2, and 6, the computing device 108 includes a computer readable medium ("CRM") 114, which may include computer storage media, communication media, and/or another available media medium that can be accessed by the processor 110. For example, CRM 114 may include non-transitory computer storage media and communication media. By way of example and not limitation, computer storage media includes memory, volatile media, nonvolatile media, removable media, and/or non-removable media implemented in a method or technology for storage of information, such as machine/computer readable/executable instructions, data structures, program modules, or other data. Communication media includes machine/computer readable/executable instructions, data structures, program modules, or other data and includes an information delivery media or system. The CRM 114 may store executable instructions for executing the NNS assessment application 300 to detect, measure, and analyze orofacial activity of a patient.

Generally, the NNS assessment application 300 includes one or more modules and sub-modules that further include routines, programs, instructions, objects, components, data structures, etc., that perform particular tasks or implement particular abstract data types or functions. In one aspect, the NNS assessment application 300 includes at least one of a self-test module 302, an error detection module 304, a data collection module 306, a data analysis module 308, and an output module 310.

In one aspect, the self-test module 302 performs a Power-On Self-Test (POST) each time the device 100 is powered on. The POST verifies that the device 100 is functioning properly, as commonly understood in the art. The error detection module 304 places the device 100 and the NNS assessment application 300 in a "critical error" state if the POST identifies an unrecoverable error. Alternately, the error detection module 304 may place the device in "critical error" state at any time when an error is detected. While in the "critical error" state, the error detection module 304 prevents or disallows the collection and assessment of orofacial activity data. The error detection module 304 also notifies the user of the error condition via the display device 116. To exit the "critical error" state, the user of the device 100 may reset and/or power cycle the device 100 to initiate a new POST.

Upon successfully completing the POST, the data collection module 306 places the device 100 and application 300 into a "data capture" state, where patient orofacial activity data is captured. At the onset of the "data capture" state, the device 100 is placed in a "paused" sub-state. In one aspect, the device 100 enters an active "sub-state", in response to activation of the control button 118A. During the "active" sub-state patient orofacial activity data is collected and sampled at a user-configurable rate. According to one embodiment, the orofacial activity data is collected and sampled for two minutes. However, the data collection period may be longer or shorter than two minutes. During the data collection, the user may optionally depress the control button 118A to transition between the "paused" and "active" sub-states. The pause of the collection of the data may be needed for any of a variety of reasons, e.g., a caretaker or a patient needing a temporary break. At the expiration of the data collection period, the application 300 transitions to a "post-capture" or "data analysis" state. In one aspect, if the user desires to end the assessment and data collection prior to the expiration of the preconfigured time period, the user may actuate and hold the control button 118A to transition to the "post-capture" state. Likewise, if a subsequent assessment is desired, the user may actuate the control button 118A to transition back to the "data capture" state for performing a new assessment.

Upon entering the "post capture" state, the data analysis module 308 processes and analyzes the captured data. During processing and analysis, data analysis module 308 determines or extracts one or more patient performance metrics based on the data and information in the patient profile. By way of example and not limitation, the patient performance metrics include the Peak Area Under Burst (pAOB), the Average Area Under Burst (aAOB), the Active-Quiescent Ratio (AQR), the Spatio-Temporal Index (STI), the number of bursts per minute, the number of NNS events per minute, and the number of NNS events per burst.

In particular, determining the peak Area Under Burst (pAOB) includes identifying each NNS burst in the assessment based on the sum of pacifier displacements and oral cavity pressure for the duration of each burst and identifying the largest pacifier displacement and oral cavity pressure measurement for display. In one aspect, a burst refers to two or more suck events in less than about 1.5 seconds, while a suck event refers to a determined oral cavity pressure or pressure resulting in compression, deflection, or deformation of the pacifier 102 greater than a particular magnitude. As an example, the particular magnitude may be above five $cmH_2O$ and is typically in a range of ten to thirty $cmH_2O$. The particular magnitude may be based on upper lip movement, lower lip movement, jaw movement, tongue movement, and/or oral cavity pressure, etc. Similarly, identifying the average Area Under Burst (aAOB) includes determining the average area under all bursts in the assessment. The Active-Quiescent Ratio (AQR) refers to the total number of seconds the patient was applying pressure within the oral cavity to compress, deflect, and/or deform the pacifier divided by the total number of seconds the patient was inactive.

The Spatio-Temporal Index (STI) is the normalized statistical difference across five bursts that are indicative of the neural maturity level. The number of bursts per minute includes the total number of bursts divided by number of minutes of data collected (e.g., two minutes), while the number of NNS events per minute includes the total number of NNS events divided by number of minutes of data collected. Similarly, the number of NNS events per burst includes the total number of NNS Events contained within the bursts divided by the number of bursts.

The output module 310 generates one or more alphanumeric output displays to the display device 116. The generated alphanumeric displays provide the user with data for one or more of the performance metrics and patient profile information as determined by the data analysis module 308. In one aspect, the output module 310 also stores data in the memory 112 and may generate a signal to one or more of the status indicators 120, to provide a visual and/or audible notification to alert the user to the status of the device 100, including errors or the completion of data analysis.

In various embodiments, the user may optionally press one or more control button 118B-D to scroll through and change the displayed metric. In another embodiment, the displayed metrics may be scrolled automatically.

Figure 7:
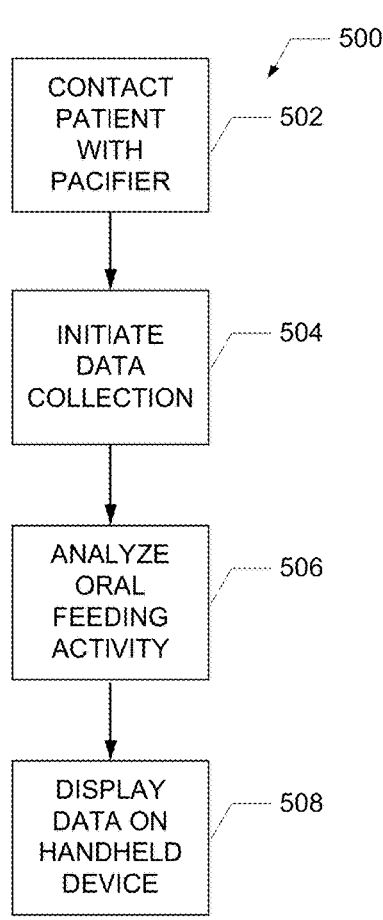
FIG. 7 is a flowchart for a method of assessing a non-nutritive suck using the handheld cordless non-nutritive suck assessment device according to one embodiment.
Figure 8:
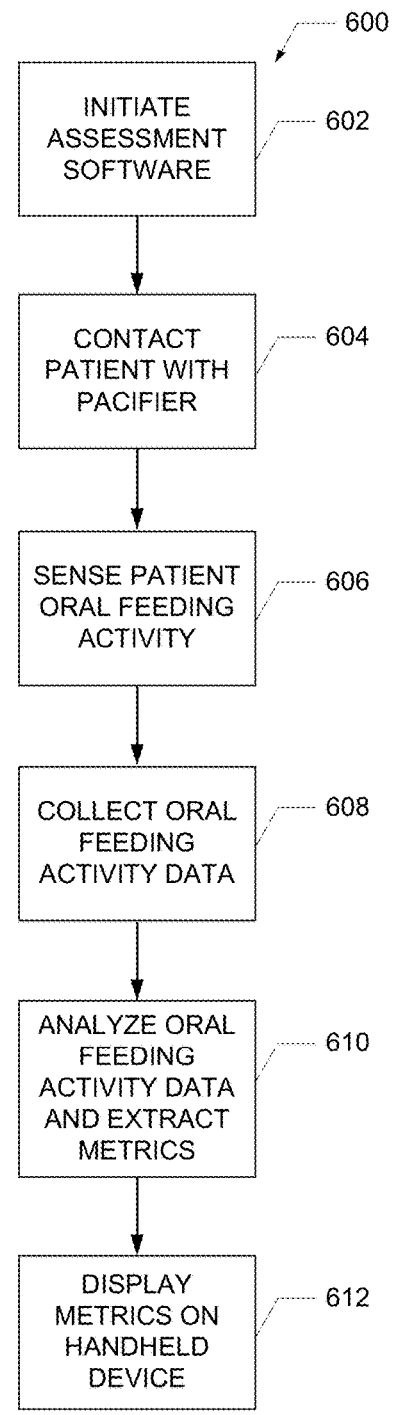
FIG. 8 is a flowchart for a method of assessing a non-nutritive suck using the handheld cordless non-nutritive suck assessment device according to one embodiment.
Figure 9:
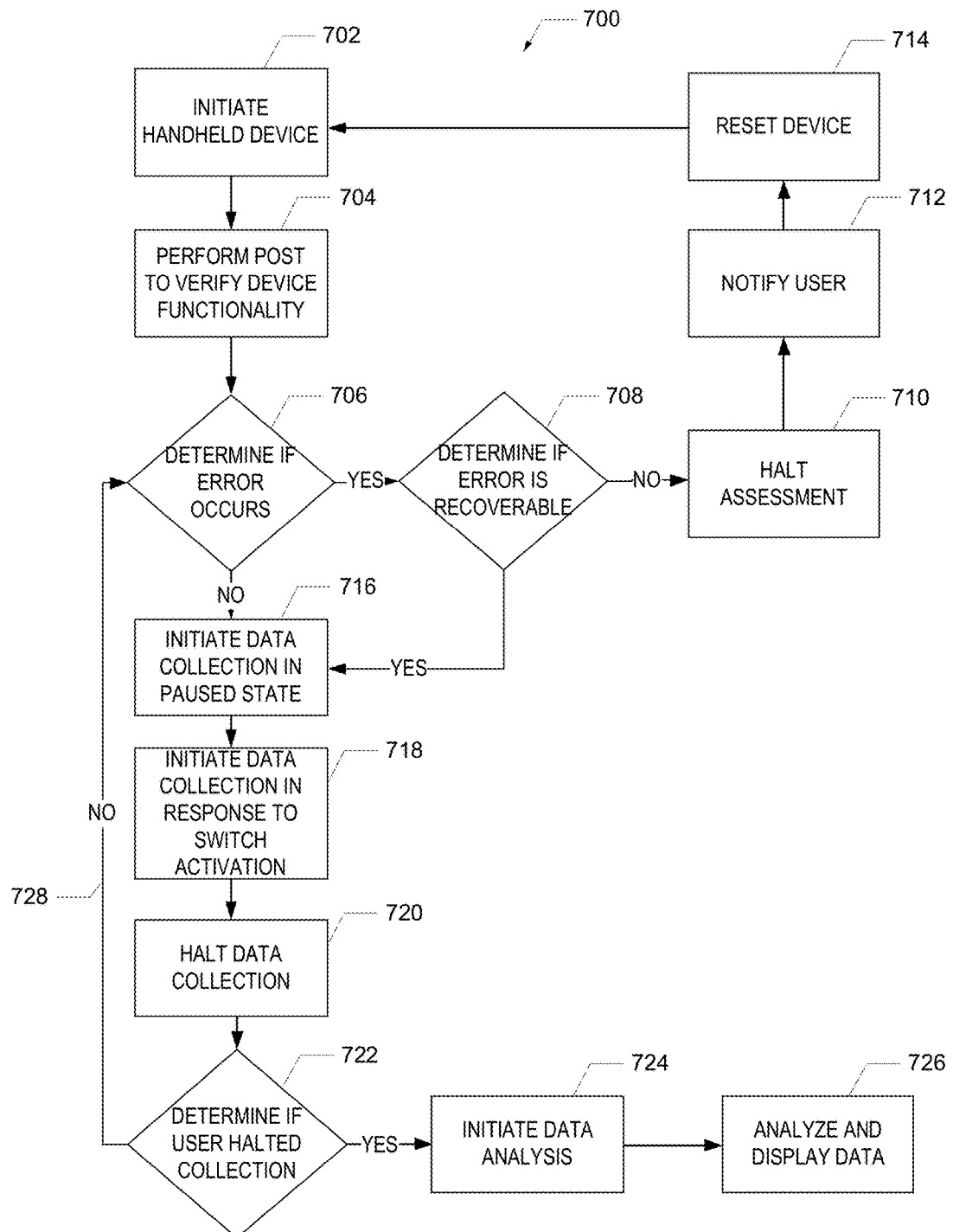
FIG. 9 is a flowchart for a method of assessing a non-nutritive suck using the handheld cordless non-nutritive suck assessment device according to one embodiment.

FIGS. 7-9 are flow-charts of various methods 500-700 for using the handheld NNS assessment device 100 to assess the orofacial activity of a patient. For example as shown in FIG. 7, in one method 500, the patient is contacted by the pacifier 102 at step 502. As an example, pacifier 102 is inserted into an oral cavity of the patient. At step 504, the user initiates data collection by actuating a control button 118. The device 102 will begin to collect and store oral cavity pressure data and pacifier pressure data. At step 506, data corresponding to the orofacial activity of the patient is collected and stored in a patient profile and analyzed to determine one or more performance metrics. The data may include data related to deformation or displacement of the pacifier caused by the patient and data related to oral cavity pressure caused by the patient. At step 508, the device 100 displays one or more performance metrics on the display device 116. In various aspects, the device displays patient profile information and the performance metrics during and/or after the data collection at step 506.

In another method 600, as shown in FIG. 8, the user initiates the execution of the NNS assessment software application 300 on the processor 110, at step 602, by actuating one or more control buttons 118. At step 604, the attached pacifier 102 is inserted into the oral cavity of the patient and brought into contact with the patient's mouth. The assessment device 100 senses an orofacial activity of the patient at step 606, and collects data corresponding to the activity at step 608 and stores the data in the memory 112 in a patient profile. The data may include information related to one or more deformation or displacement of the pacifier caused by the patient and data related to oral cavity pressure caused by the patient. At step 610, the NNS assessment software application 300 analyzes the orofacial activity data received at the processor 110 to determine one or more performance metrics and displays patient profile information and/or one or more performance metrics as determined by the NNS assessment software application 300 on the display device 116 at step 612.

FIG. 9 is a flow-chart depicting another method 700 of executing the NNS assessment software application 300, collecting orofacial activity data, and displaying the activity data for review. In one aspect, the user initiates or powers on the handheld device 100 and initiates the execution of the NNS assessment software application 300 by the processor 110 at step 702. At step 704, the self-test module 302 performs a POST to verify the functionality of the device 100. At step 706, the error-detection module 302 determines if an error in the initiation of the device 100 or the application 300 has occurred. If an error has occurred, the error-detection module 302 determines, at step 708, if the device 100 or application 300 can recover from the error identified at step 706. If the error is not recoverable, the error-detection module 302 stops execution of the application 300 at step 710, notifies the user via the display device 116 at step 712, and then resets the device 100 at step 714. If the device 100 is reset in step 714, then the device 100 initiates the execution of the NNS assessment software application by the processor 100 at step 702 and the method 700 begins again.

Conversely, if the error-detection module 302 determines that no error has occurred at step 706 or determines that the error is recoverable at step 708, the data collection module 306 initiates a data collection state in a paused sub-state at step 716. In response to an actuation of the control button 118A by the user at step 718, the data collection module 306 exits the paused sub-state and enters an active sub-state. In the active sub-state, the data collection module is configured to receive patient orofacial activity and store data associated with the patient orofacial activity in the memory 112 in a patient profile. The data may include pacifier pressure data related to deformation or displacement of the pacifier caused by the patient and data related to oral cavity pressure caused by the patient. At step 720, the data collection module 306 stops collecting and storing data and determines, at step 722, if orofacial activity data is still being generated at the pacifier 102 and received at the processor 110. If the data collection module 306 determines that the data collection was caused by the user, whether through actuation of the control button 118A or by expiration of a pre-determined time period, the stored orofacial activity data is analyzed by the data analysis module 308 at step 724 to determine one or more performance metrics. At step 726, patient profile information and one or more orofacial activity performance metrics are displayed on the display device 116. However, if the termination of data collection was not caused by the user, the method step 700 returns to block step 706 if an error has occurred.

Figure 10:
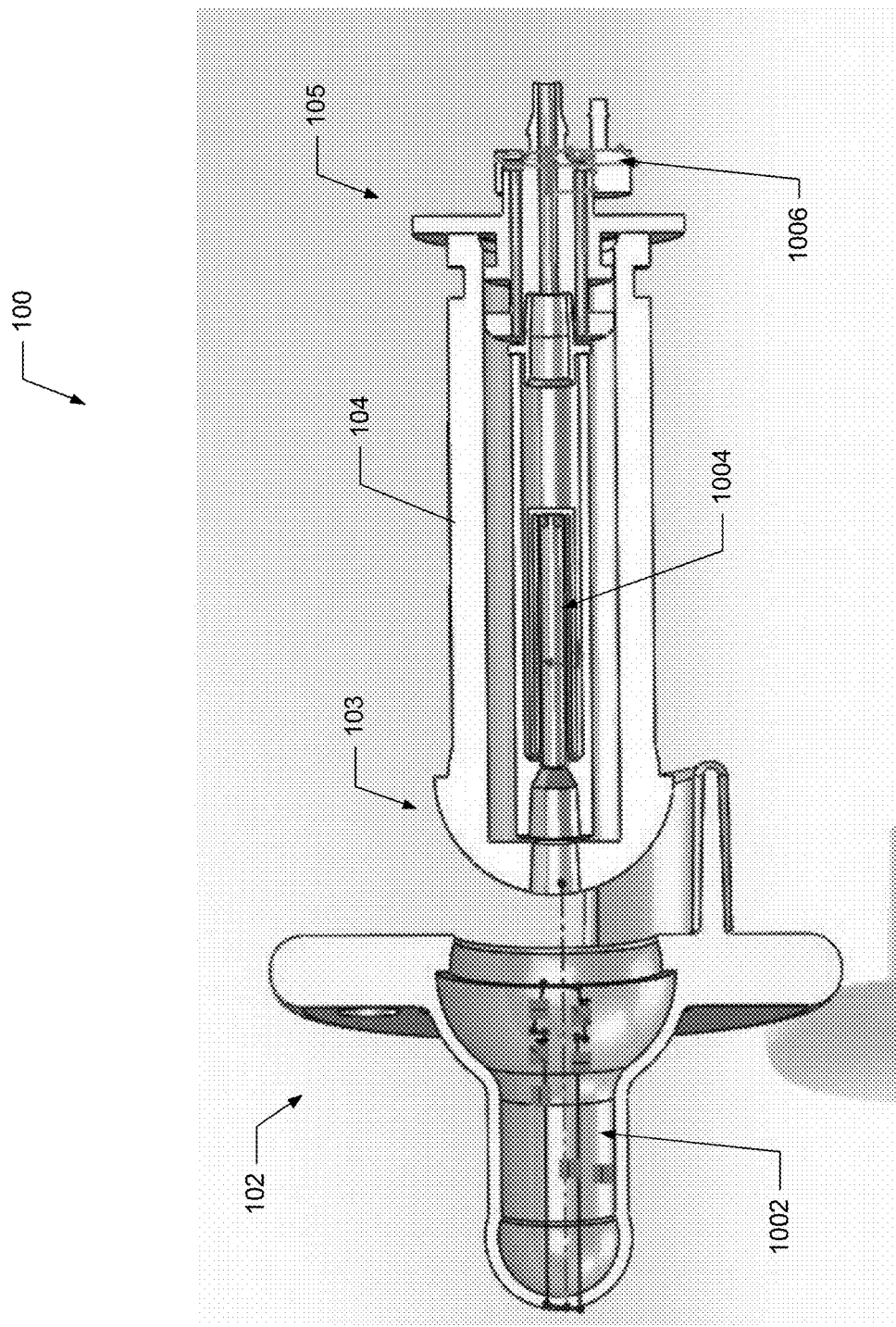
FIG. 10 is a cross-sectional view of the handheld cordless non-nutritive suck assessment device according to one embodiment.

FIG. 10 shows a cross-sectional view of the device 100 according to an example embodiment. As shown in FIG. 10, the pacifier 102 includes an open annular tube 1002 to measure oral cavity pressure using a first pressure sensor 1004 and senses compression measurement using a second pressure sensor 1006. According to one embodiment, the open annular tube 1002 is a tube with a male luer fitting that engages and is in fluid communication with the adaptor 104. The distal end 103 of the pacifier adaptor 104 is shown as engaged to the pacifier 102 and the proximal end of the adaptor 105 may be engaged to the housing 106. The oral cavity pressure and the compression of the pacifier are measured by the one or more sensors 1004 and 1006 that may be disposed in the adapter 104 In one embodiment, the sensors 1004 and 1006 are in further communication with one or more transducers 122.

Figure 12:
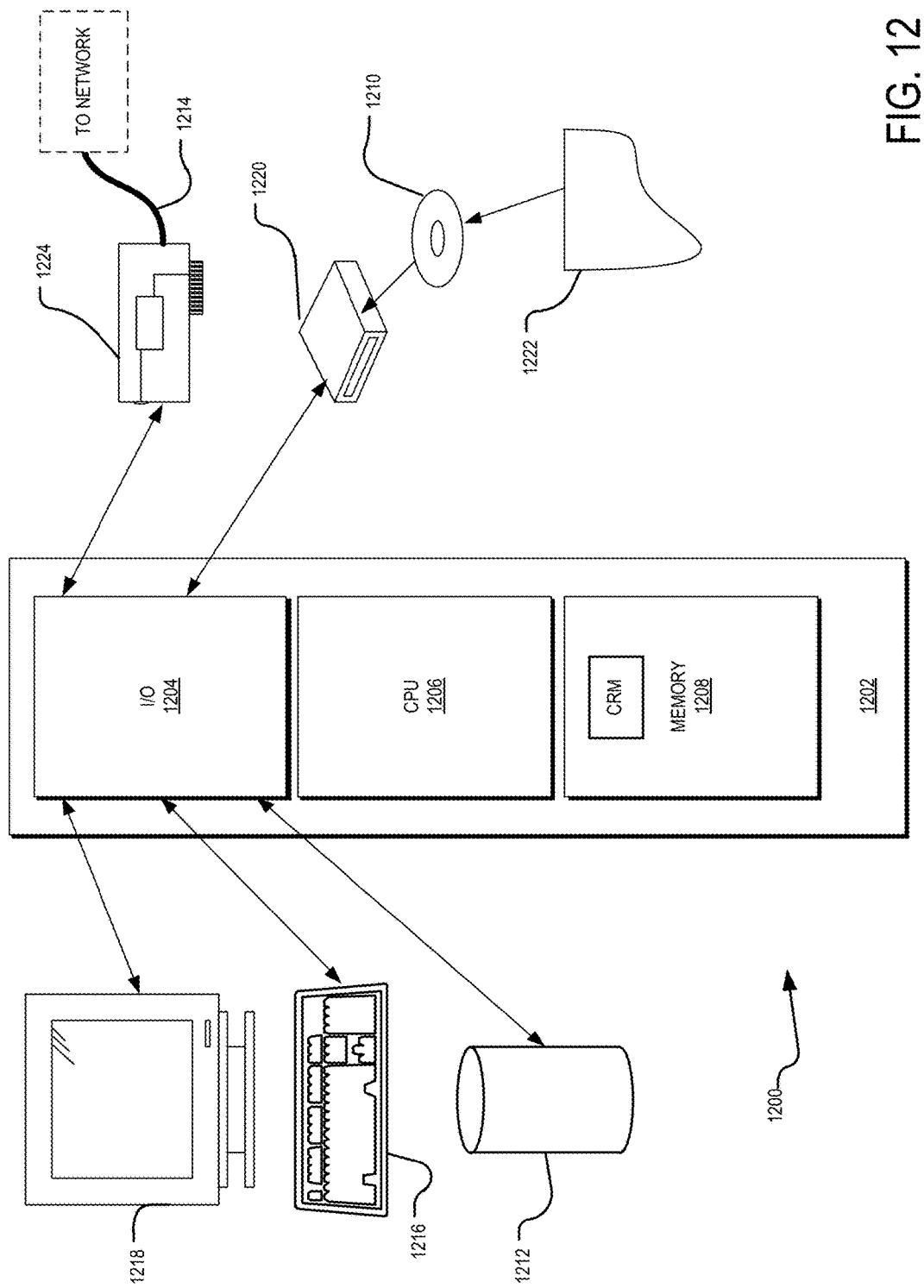
FIG. 12 illustrates a block diagram of an example computer device for use with the example embodiments.

FIG. 12 illustrates an example computing system 1200 that may implement various systems, such as the computing device 108, and methods discussed herein, such as processes 500, 600, and 700. A general purpose computer system 1200 is capable of executing a computer program product to execute a computer process. Data and program files may be input to the computer system 1200, which reads the files and executes the programs therein such as the NNS assessment application 300 having the self-test module 302, the error detection module 304, the data collection module 306, the data analysis module 308, and the output module 310. Some of the elements of a general purpose computer system 1200 are shown in FIG. 12 wherein a processor 1202 is shown having an input/output (I/O) section 1204, a central processing unit (CPU) 1206, and a memory section 1208. There may be one or more processors 1202, such that the processor 1202 of the computer system 1200 comprises a single central-processing unit 1206, or a plurality of processing units, commonly referred to as a parallel processing environment. The computer system 1200 may be a conventional computer, a server, a distributed computer, or any other type of computer, such as one or more external computers made available via a cloud computing architecture. The presently described technology is optionally implemented in software devices loaded in memory 1208, stored on a configured DVD/CD-ROM 1210 or storage unit 1212, and/or communicated via a wired or wireless network link 1214, thereby transforming the computer system 1200 in FIG. 12 to a special purpose machine for implementing the described operations.

The memory section 1208 may be volatile media, non-volatile media, removable media, non-removable media, and/or other media or mediums that can be accessed by a general purpose or special purpose computing device. For example, the memory section 1208 may include non-transitory computer storage media and communication media. Non-transitory computer storage media further may include nonvolatile, removable, and/or non-removable media implemented in a method or technology for the storage (and retrieval) of information, such as computer/machine-readable/executable instructions, data and data structures, engines, program modules, and/or other data. Communication media may, for example, embody computer/machine-readable/executable, data structures, program modules, algorithms, and/or other data.

The I/O section 1204 is connected to one or more user-interface devices (e.g., a keyboard 1216 and a display unit 1218), a disc storage unit 1212, and a disc drive unit 1220. Generally, the disc drive unit 1220 is a DVD/CD-ROM drive unit capable of reading the DVD/CD-ROM medium 1210, which typically contains programs and data 1222. Computer program products containing mechanisms to effectuate the systems and methods in accordance with the presently described technology may reside in the memory section 1204, on a disc storage unit 1212, on the DVD/CD-ROM medium 1210 of the computer system 1200, or on external storage devices made available via a cloud computing architecture with such computer program products, including one or more database management products, web server products, application server products, and/or other additional software components. Alternatively, a disc drive unit 1220 may be replaced or supplemented by a floppy drive unit, a tape drive unit, or other storage medium drive unit. The network adapter 1224 is capable of connecting the computer system 1200 to a network via the network link 1214, through which the computer system can receive instructions and data. Examples of such systems include personal computers, Intel or PowerPC-based computing systems, AMD-based computing systems and other systems running a Windows-based, a UNIX-based, or other operating system. It should be understood that computing systems may also embody devices such as Personal Digital Assistants (PDAs), mobile phones, tablets or slates, multimedia consoles, gaming consoles, set top boxes, etc.

When used in a LAN-networking environment, the computer system 1200 is connected (by wired connection and/or wirelessly) to a local network through the network interface or adapter 1224, which is one type of communications device. When used in a WAN-networking environment, the computer system 1200 typically includes a modem, a network adapter, or any other type of communications device for establishing communications over the wide area network. In a networked environment, program modules depicted relative to the computer system 1200 or portions thereof, may be stored in a remote memory storage device. It is appreciated that the network connections shown are examples of communications devices for and other means of establishing a communications link between the computers may be used.

In an example implementation, source code executed by the computing device 108, a plurality of internal and external databases, source databases, and/or cached data on servers are stored in memory 112 of the computing device 108, the memory 1108 or other storage systems, such as the disk storage unit 1212 or the DVD/CD-ROM medium 1210, and/or other external storage devices made available and accessible via a network architecture. The source code executed by the computing device 108 may be embodied by instructions stored on such storage systems and executed by the processor 1202.

Some or all of the operations described herein may be performed by the processor 1202, which is hardware. Further, local computing systems, remote data sources and/or services, and other associated logic represent firmware, hardware, and/or software configured to control operations of the handheld NNS assessment device 100 and/or other components. Such services may be implemented using a general purpose computer and specialized software (such as a server executing service software), a special purpose computing system and specialized software (such as a mobile device or network appliance executing service software), or other computing configurations. In addition, one or more functionalities disclosed herein may be generated by the processor 1202 and a user may interact with a Graphical User Interface (GUI) using one or more user-interface devices (e.g., the keyboard 1216, the display unit 1218, and the user devices 1204) with some of the data in use directly coming from online sources and data stores. The system set forth in FIG. 12 is but one possible example of a computer system that may employ or be configured in accordance with aspects of the present disclosure.

In the present disclosure, the methods disclosed may be implemented as sets of instructions or software readable by a device. Further, it is understood that the specific order or hierarchy of steps in the methods disclosed are instances of example approaches. Based upon design preferences, it is understood that the specific order or hierarchy of steps in the method can be rearranged while remaining within the disclosed subject matter. The accompanying method claims present elements of the various steps in a sample order, and are not necessarily meant to be limited to the specific order or hierarchy presented.

The described disclosure may be provided as a computer program product, or software, that may include a non-transitory machine-readable medium having stored thereon executable instructions, which may be used to program a computer system (or other electronic devices) to perform a process according to the present disclosure. A non-transitory machine-readable medium includes any mechanism for storing information in a form (e.g., software, processing application) readable by a machine (e.g., a computer). The non-transitory machine-readable medium may include, but is not limited to, magnetic storage medium (e.g., floppy diskette), optical storage medium (e.g., CD-ROM); magneto-optical storage medium, read only memory (ROM); random access memory (RAM); erasable programmable memory (e.g., EPROM and EEPROM); flash memory; or other types of medium suitable for storing electronic executable instructions.

It is believed that the present disclosure and many of its attendant advantages will be understood by the foregoing description, and it will be apparent that various changes may be made in the form, construction, and arrangement of the components without departing from the disclosed subject matter or without sacrificing all of its material advantages. The form described is merely explanatory, and it is the intention of the following claims to encompass and include such changes.

While the present disclosure has been described with reference to various embodiments, it will be understood that these embodiments are illustrative and that the scope of the disclosure is not limited to them. Many variations, modifications, additions, and improvements are possible. More generally, embodiments in accordance with the present disclosure have been described in the context of particular implementations. Functionality may be separated or combined in blocks differently in various embodiments of the disclosure or described with different terminology. These and other variations, modifications, additions, and improvements may fall within the scope of the disclosure as defined in the claims that follow.

What is claimed is:

1. A handheld device for a non-nutritive suck (NNS) assessment of a patient comprising:
   a device housing containing a non-nutritive suck assessment system, wherein the non-nutritive suck assessment system comprises:
      one or more transducers to determine a pacifier displacement caused by the patient and to generate a first electrical signal in response to at least one compression of a pacifier engaged to the device and determine an oral cavity pressure caused by the patient and to generate a second electrical signal in response to the oral cavity pressure;
      an analog to digital convertor to convert the first electrical signal and the second electrical signal to NNS data received at a processor of the non-nutritive suck assessment system;
      memory to store the NNS data collected from the pacifier and a suck assessment application, wherein the suck assessment application includes instructions executable by the processor;
      one or more switches to control the operation of the handheld device, to control execution of the suck assessment application, and to control a display of assessment data on a display device engaged to the device housing;
      at least one status indicator light; and
      a power source; and
   the handheld device further comprising a pacifier adapter configured to connect the device housing to a pacifier, wherein the pacifier adapter is dimensioned to maintain separation of the pacifier and the one or more transducers, wherein the pacifier is removably attached to the pacifier adapter.

2. The handheld device of claim 1, wherein the handheld device is cordless.

3. The handheld device of claim 1 further comprising at least one signal conditioning circuit to filter and amplify the first electrical signal and the second electrical signal generated by the one or more transducers.

4. The handheld device of claim 1 wherein the power source is a rechargeable battery, and the handheld device further comprising:
   a battery charging circuit, wherein the battery charging circuit is configured to engage an external power supply.

5. The handheld device of claim 1 further comprising:
   a wireless transceiver to transmit the NNS data collected from the pacifier, the suck assessment application, and at least one performance metric to a computing device.

6. The handheld device of claim 1 wherein the suck assessment application comprises:
   a self-test module to perform a Power-On Self-Test;
   an error-detection module to detect an error in an operation of the suck assessment application and provide a notification of the error;
   a data collection module to receive patient oral feeding activity data within the NNS data;
   a data analysis module to analyze the patient oral feeding activity data and to determine at least one patient performance metric; and
   an output module to generate one or more data displays on the display device.

7. The handheld device of claim 6, wherein the at least one patient performance metric comprises at least one of a peak area under burst, an average area under burst, an active-quiescent ratio, a spatio-temporal index, a rate of bursts per minute, a rate of non-nutritive suck events per minute, and a rate of non-nutritive suck events per burst.

8. The handheld device of claim 1, wherein:
   the pacifier adaptor has a first end in fluid communication with the transducer engaged to the device housing and a second end in fluid communication with the pacifier and the pacifier adaptor defining a lumen.

9. The handheld device of claim 8, wherein the pacifier adaptor has a length between 2.125" and 2.25" to provide a sterile barrier between the handheld device and the patient.

10. The handheld device of claim 1, wherein the display device is a liquid crystal display.

11. The handheld device of claim 1, wherein the display device is integrated with the device housing.

12. The handheld device of claim 1, wherein the memory comprises persistent random access memory.

13. A handheld device for non-nutritive suck assessment in a patient, the device comprising:
   a housing containing a computing device having at least one processor and memory;
   a pacifier adaptor having a proximal end and a distal end, wherein the pacifier adaptor defines a lumen between the proximal end and the distal end and the proximal end is mechanically engaged to the device housing;
   a pacifier removably attached to the distal end of the pacifier adaptor to contact the patient and induce an oral feeding activity in the patient;
   a suck assessment application executed by the at least one processor, the suck assessment application to identify the oral feeding activity of the patient and determine at least one oral feeding metric selected from a group consisting of a peak area under burst, an average area under burst, an active-quiescent ratio, a spatio-temporal index, a rate of bursts per minute, a rate of non-nutritive suck events per minute, and a rate of non-nutritive suck events per burst;
   a display device connected to the housing;
   at least one control switch connected to the housing; and
   one or more status indicator lights connected to the housing.

14. The handheld device of claim 13 further comprising the pacifier connected to the pacifier adaptor.

15. The handheld device of claim 13, wherein the display device is integrated with the device housing.

16. A method for using a cordless handheld device comprising at least one processor, memory, a pacifier, a transducer, a control button, and a display to assess oral feeding activity in a patient, the method comprising:
   contacting the pacifier with the patient;
   actuating the control button to collect oral feeding activity data at the processor;
   analyzing, by at least one processor, the oral feeding activity data to identify at least one metric of the oral feeding activity, wherein the metric is at least one member of a group consisting of a peak area under burst, an average area under burst, an active-quiescent ratio, a spatio-temporal index, a rate of bursts per minute, a rate of non-nutritive suck events per minute, and a rate of non-nutritive suck events per burst; and
   displaying, by the at least one processor, the at least one metric on the display.

17. A method for assessing a non-nutritive suck of a patient using a handheld device comprising a non-nutritive suck assessment system, the method comprising:
   actuating a control button to initiate execution of a non-nutritive suck assessment application on a processor of the handheld device;
   contacting a pacifier engaged to the handheld device with the patient;
   sensing, by at least one processor, patient oral feeding activity at a data collection module of a non-nutritive suck assessment application, the patient activity identified by a transducer in communication with the pacifier;
   collecting, by the at least one processor, patient oral feeding activity data at the data collection module of the non-nutritive suck assessment application;
   extracting, by the at least one processor, at least one patient performance metric from the patient oral feeding activity data at a data analysis module of the non-nutritive suck assessment application; and
   displaying, by the at least one processor, patient performance data, the performance data based on the at least one patient performance metric on a display of the handheld device.

18. The method of claim 17 further comprising performing a power-on self-test before contacting the patient.

19. The method of claim 17 further comprising:
   actuating a first display control button to scroll through the patient performance data in a first direction; and
   actuating a second display control button to scroll through the patient performance data in a second direction.

20. The method of claim 17 further comprising storing the patient performance data in a persistent random access memory of the non-nutritive suck assessment system.

21. The method of claim 17 further comprising exporting the patient performance data to a data storage device.

22. A method for assessing a non-nutritive suck, comprising:
- simultaneously receiving, by at least one processor, a pacifier pressure responsive to one of compression, deformation, displacement, and deflection of a pacifier, and an oral cavity pressure responsive to a pressure in an open annular tube in the pacifier;
- generating, by the at least one processor, a first electrical signal responsive to the pacifier pressure and a second electrical signal responsive to the oral cavity pressure;
- converting, by the at least one processor, the first electrical signal and the second electrical signal into non-nutritive suck (NNS) information representing a NNS session;
- displaying, by the at least one processor, output responsive to the NNS information; and
- analyzing, by the at least one processor, the ratio of pacifier pressure to oral cavity pressure as a function of time during the NNS session to determine at least one of a peak area under burst, an average area under burst, an active-quiescent ratio, a spatio-temporal index, a rate of bursts per minute, a rate of non-nutritive suck events per minute, and a rate of non-nutritive suck events per burst.

23. The method of claim 22, further comprising
storing, by the at least one processor, the NNS information in a patient profile, the patient profile including a patient name, a patient age, and a ratio of pacifier pressure to oral cavity pressure as a function of time during the NNS session.

24. The method of claim 23, further comprising:
determining, by the at least one processor, based on the ratio of pacifier pressure to oral cavity pressure as a function of time during the non-nutritive suck session, a maximum pacifier pressure value, a minimum pacifier pressure value, a maximum oral cavity pressure value, and a minimum oral cavity pressure value.

25. The method of claim 22, wherein the NNS session is two minutes in duration.

* * * * *